(12) United States Patent
Krishnamachari et al.

(10) Patent No.: US 10,386,303 B2
(45) Date of Patent: Aug. 20, 2019

(54) RAMAN MICROSCOPIC IMAGING DEVICE

(71) Applicant: LEICA MICROSYSTEMS CMS GMBH, Wetzlar (DE)

(72) Inventors: Vishnu Vardhan Krishnamachari, Seeheim-Jugenheim (DE); Volker Seyfried, Nussloch (DE); William C. Hay, Heppenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 15/037,455

(22) PCT Filed: Nov. 19, 2014

(86) PCT No.: PCT/EP2014/075049
§ 371 (c)(1),
(2) Date: Aug. 22, 2016

(87) PCT Pub. No.: WO2015/075084
PCT Pub. Date: May 28, 2015

(65) Prior Publication Data
US 2016/0363537 A1    Dec. 15, 2016

(30) Foreign Application Priority Data

Nov. 19, 2013   (DE) .................. 10 2013 112 759

(51) Int. Cl.
*G01N 21/65* (2006.01)
*G01J 3/44* (2006.01)
(Continued)

(52) U.S. Cl.
CPC ............ *G01N 21/65* (2013.01); *G01J 3/0227* (2013.01); *G01J 3/10* (2013.01); *G01J 3/44* (2013.01); *G01N 2021/655* (2013.01)

(58) Field of Classification Search
CPC .................................. G01N 21/65; G01J 3/44
See application file for complete search history.

(56) References Cited

U.S. PATENT DOCUMENTS 4,505,586 A    3/1985 Tochigi et al.
6,560,478 B1 * 5/2003 Alfano ................. A61B 5/0075
                                                          600/473

(Continued)

OTHER PUBLICATIONS

Nandakumar, et al., Vibrational imaging based on stimulated Raman scattering microscopy, New Journal of Physics, vol. 11, p. 033026, pp. 1-9 Mar. 25, 2009.

(Continued)

*Primary Examiner* — Maurice C Smith
(74) *Attorney, Agent, or Firm* — Hodgson Russ LLP (57) ABSTRACT

A Raman microscopy imaging device (100) is described, having: a first laser light source (12) for emitting a first laser beam (16) having a first wavelength along a first light path (20); a second laser light source (44) for emitting a second laser beam (18) having a second wavelength, different from the first wavelength, along a second light path (22) physically separated from the first light path (20); a beam combining element (32) for collinearly combining the two laser beams (16, 18) in one shared light path (34) directed onto a sample; a detector (38) for sensing a measured signal on the basis of the two laser beams (16, 18) interacting with the sample; and an evaluation unit (40) for evaluating the measured signal sensed by the detector (38). According to the present invention the first laser light source (12) is embodied as a pulsed source, and the second laser light source (44) as a continuous source.

11 Claims, 4 Drawing Sheets

(51) Int. Cl.
  *G01J 3/02* (2006.01)
  *G01J 3/10* (2006.01)

(56) References Cited

U.S. PATENT DOCUMENTS

| | | | |
|---|---|---|---|
| 2010/0188496 A1* | 7/2010 | Xie | G01J 3/10 348/79 |
| 2013/0162994 A1* | 6/2013 | Xie | G01N 21/171 356/342 |
| 2014/0132955 A1 | 5/2014 | Kawano et al. | |
| 2014/0247448 A1* | 9/2014 | Wise | G01N 21/65 356/301 |
| 2014/0253918 A1* | 9/2014 | Ozeki | G01J 3/4412 356/301 |

OTHER PUBLICATIONS

Freudiger, et al., Optical Heterodyne-Detected Raman-Induced Kerr Effect (OHD-RIKE) Microscopy, The Journal of Physical Chemistry B, vol. 115, pp. 5574-5581 Apr. 19, 2011.

Slipchenko, et al., Heterodyne detected nonlinear optical imaging in a lock-in free manner, Journal of Biophotonics, vol. 5, No. 10, pp. 801-807 Mar. 5, 2012.

Zumbusch, et al., Three-Dimensional Vibrational Imaging by Coherent Anti-Stokes Raman Scattering, Physical Review Letters, vol. 82, No. 20, pp. 4142-4145 May 17, 1999.

Cheng, et al., Coherent Anti-Stokes Raman Scattering Microscopy: Instrumentation, Theory, and Applications, Journal of Physical Chemistry B, vol. 108, pp. 827-840 Dec. 25, 2003.

Evans, et al., Coherent Anti-Stokes Raman Scattering Microscopy: Chemical Imaging for Biology and Medicine, Annual Review of Analytical Chemistry, vol. 1, pp. 883-909 Jul. 1, 2008.

Saar, et al., Video-Rate Molecular Imaging in Vivo with Stimulated Raman Scattering, Science, vol. 330, No. 6009, pp. 1368-1370 Dec. 3, 2010.

International Searching Authority, Written Opinion of the International Searching Authority for PCT/EP2014/075049 May 28, 2015.

Eesley, Coherent Raman Spectroscopy, Journal of Quantitative Spectroscopy and Radiative Transfer, vol. 22, pp. 507-576 Jan. 31, 1979.

\* cited by examiner

RAMAN MICROSCOPIC IMAGING DEVICE

CROSS-REFERENCE TO RELATED APPLICATIONS

The present application is the U.S. national phase of International Application No. PCT/EP2014/075049 filed Nov. 19, 2014, which claims priority of German Application No. 10 2013 112 759.2 filed Nov. 19, 2013, the entirety of which is incorporated herein by reference.

FIELD OF THE INVENTION

The invention relates to a Raman microscopy imaging device, having a first laser light source for emitting a first laser beam having a first wavelength along a first light path; a second laser light source for emitting a second laser beam having a second wavelength, different from the first wavelength, along a second light path physically separated from the first light path; a beam combining element for collinearly combining the two laser beams in one shared light path directed onto a sample; a detector for sensing a measured signal on the basis of the two laser beams interacting with the sample; and an evaluation unit for evaluating the measured signal sensed by the detector. The invention further relates to a Raman microscopy imaging method.

BACKGROUND OF THE INVENTION

Coherent Raman scattering microscopy (abbreviated "CRSM") has recently acquired considerable importance in image-producing chemical sample analysis, for example in biology, pharmacy, or food science. A variety of CRSM methods are utilized, for example stimulated Raman scattering (SRS), coherent anti-Stokes Raman scattering (CARS), and Raman-induced Kerr effect scattering (RIKES). The list of documents below will be referred to hereinafter regarding the existing art:

[1] Nandakumar, P., Kovalev, A., Volkmer, A.: "Vibrational imaging based on stimulated Raman scattering microscopy," New Journal of Physics, 2009, 11, 033026.
[2] Freudiger, C. W., Roeffaers, M. B. J., Zhang, X., Saar, B. G., Min, W., Xie, X. S.: "Optical heterodyne-detected Raman-induced Kerr effect (OHD-RIKE) microscopy," Journal of Physical Chemistry B, 2011, 115, 5574-5581.
[3] Saar, B. G., Freudiger, C. W., Reichman, J., Stanley, C. M., Holtom, G. R., Vie, X. S.: "Video-rate molecular imaging in vivo with stimulated Raman scattering," Science, 2010, 330, 1368-1370.
[4] Mikhail N. Slipchenko, Robert A. Oglesbee, Delong Zhang, Wei Wu, Ji-Xin Cheng: "Heterodyne detected nonlinear optical imaging in a lock-in free manner," J. Biophotonics, 2012, 5, 1-7.
[5] Zumbusch, A., Holtom, G. R., Xie, X. S.: "Three-dimensional vibrational imaging by coherent anti-Stokes Raman scattering," Phys. Rev. Lett., 1999, 82, 4142-4145.
[6] Cheng, J. X. and Xie, X. S.: "Coherent anti-Stokes Raman scattering microscopy: Instrumentation, theory, and applications," J. Phys. Chem. B, 2004, 108, 827-840.
[7] Evans, C. L. and Xie, X. S.: "Coherent anti-Stokes Raman scattering microscopy: chemical imaging for biology and medicine," Annu. Rev. Anal. Chem., 2008, 1, 883-909.

In the CRSM technique, two pulsed light fields having pulse widths in a range from 100 fs to 20 ps, of different wavelengths, are directed through a confocal microscope optical system and focused onto the sample. The pulsed light fields are emitted onto the sample at frequencies that are typically in a range from 1 to 100 MHz. The light fields are spatially and temporally superimposed on one another on the sample via corresponding beam guidance and suitable focusing optics. In the SRS method or the image-producing superimposed RIKES method, for example, one of the two light fields is modulated in terms of intensity, frequency, or polarization at a specific frequency that is typically in the kHz to MHz range, before interacting in the sample with the other light field. For SRS and RIKES image production, the initially unmodulated light field is then sensed and, using a lock-in technique or envelope curve demodulation technique, the intensity modulation is extracted and presented in the form of an image. Reference is made to documents [1], [2], and [3] regarding implementation of the lock-in technique. The envelope curve demodulation technique is described in document [4]. In the case of CARS and CSRS a third light field is sensed as a consequence of interaction with the sample, and displayed as an image. This is described in documents [5], [6], and [7].

In all the CRSM techniques recited above, the measured signal is strong only if the difference between the frequencies of the incident light fields coincides with a vibrational resonance frequency in the sample. At present the best images in terms of spectral selectivity, signal intensity, and signal to noise ratio are obtained using picosecond laser light sources and optical parametric oscillators (OPOs) having pulse widths from 5 to 7 ps.

Among the various image-producing techniques based on coherent Raman scattering, the SRS image-producing method has attracted particular attention in the recent past because of the resonance-free background that is not present in the images. Because of the modulation and demodulation techniques explained above that are utilized in the SRS method, however, this method is also very sensitive in terms of the delay that must be established between the laser beams emitted from the two pulsed laser light source, in terms of the pulse synchronization that must exist during operation of the two pulsed laser light sources, and in terms of the time-related cyclical "jitter" that often occurs when the pulsed laser light sources are operated. A typical SRS image-producing device is moreover comparatively costly, and is limited with regard to its application capabilities.

It has therefore been proposed that in SRS imaging, the two pulsed laser light sources be replaced with continuous sources. In this case as well, one of the two laser beams is amplitude-modulated by means of a modulator. Although a solution of this kind is inexpensive, the resulting SRS measured signal is at least $10^6$ times weaker than the measured signal obtained with the aid of pulsed laser light sources. It is evident from this that a device operating according to the SRS method with two continuous laser light sources is unsuitable for real-time image generation, in which approximately 25 individual images must be generated every second. In addition, continuous laser light sources adjustable over a broad wavelength band are in any case not yet readily available at this time.

SUMMARY OF THE INVENTION

An object of the invention is to describe a Raman microscopy imaging device that can be implemented inexpensively and nevertheless in a reliably operating fashion. A further object of the invention is to describe a corresponding Raman microscopy imaging method.

The invention achieves this object by way of the subject matter of the independent claims. Advantageous refinements are described in the dependent claims.

The invention makes provision, in the context of a device of the kind described previously, to embody the first laser light source as a pulsed source that outputs the first laser beam in the form of a pulsed laser beam, while the second laser light source is embodied as a continuous source that emits the second laser beam in the form of a continuous laser beam.

The first laser beam emitted from the pulsed source according to the present invention is intrinsically amplitude-modulated as a pulsed beam. With the device according to the present invention it is therefore no longer necessary to provide a modulator intended specifically for amplitude modulation. A high-frequency driver required in the existing art for application of control to the modulator can correspondingly also be omitted.

Embodying the second laser light source as a continuous source, also referred to as a "CW" source, in turn makes it possible to omit the delay stage that is usual in the existing art. The device according to the present invention thus makes do with a smaller number of optical elements, e.g. mirrors, so that light losses are also avoided.

In the context of application of the approach according to the present invention to the SRS method, the sensed measured signal is based on the originally continuous laser beam. Undesired intensity peaks in the measured signal, which can occur when two pulsed laser light sources are used, are thus avoided. It is therefore also not necessary to provide in the evaluation unit a precise low-pass filtering function with which the intensity peaks in the measured signal can be filtered out.

Continuously operating laser light sources that exhibit outstanding beam quality as well as high stability over time are obtainable at comparatively low cost. The embodiment according to the present invention of one of the two laser light sources in the form of a continuously operating source is consequently advantageous not only from the standpoint of cost but also in terms of beam quality and stability over time. It can be expected that noise in the sensed measured signal will be low.

Pulsed laser light sources having an adjustable wavelength are often furnished together with commercially usual optical systems, for example confocal laser scanning microscopes, in order to enable a variety of image-producing applications. Imaging methods based on the principle of frequency doubling (SHG) or frequency tripling (THG) may be mentioned here purely by way of example. Two-photon microscopy (TPEF) also represents a possible application. A system designed for such an application can thus be expanded in order to implement the approach according to the present invention with no need to provide additional laser light sources.

An optical filter that blocks the first laser beam and directs the second laser beam onto the detector is preferably arranged in front of the detector. The device according to the present invention is thereby configured, for example, to carry out the SRS method, in which an amplitude modulation of the second laser beam, which modulation acts upon the second laser beam as a consequence of the interaction of the two laser beams with the sample, is sensed as a measured signal.

The evaluation unit is embodied, for example, in such a way that it evaluates the measured signal as a function of a reference signal that corresponds to a pulse repetition rate at which the first laser light source emits the pulsed first laser beam.

The device according to the present invention preferably contains a reference signal generator that generates the reference signal, corresponding to the pulse repetition rate, on the basis of the first laser beam emitted from the first laser source and delivers it to the evaluation unit. The pulse generator can be contained in the pulsed source itself. Alternatively, it is embodied as a separate subassembly.

If the reference signal generator constitutes a separate unit it encompasses, for example, a beam splitter arranged in the first light path for splitting off a portion of the first laser beam emitted from the pulsed source; a rate detector for sensing the pulse repetition rate of the pulsed source on the basis of the first laser beam split off by the beam splitter; and a signal shaper for generating the reference signal as a function of the sensed pulse repetition rate.

A femtosecond laser or a picosecond laser is preferably used as a pulsed source. The device according to the present invention can thus be used profitably in a CRSM method in which, as explained previously, pulse widths in a range from 100 fs to 20 ps are utilized.

The approach according to the present invention is particularly advantageously suitable for carrying out the SRS method. It is not limited thereto, however, and can likewise be applied to other methods such as CARS, CSRS, or RIKES.

BRIEF DESCRIPTION OF THE DRAWING VIEWS

The invention will be explained below on the basis of an exemplifying embodiment with reference to the Figures, in which.

DETAILED DESCRIPTION OF THE INVENTION

Firstly an SRS imaging device not covered by the invention will be described as a comparative example with reference to FIGS. 1 and 2, and then the approach according to the present invention will be explained on the basis of that comparative example.

Figure 1:
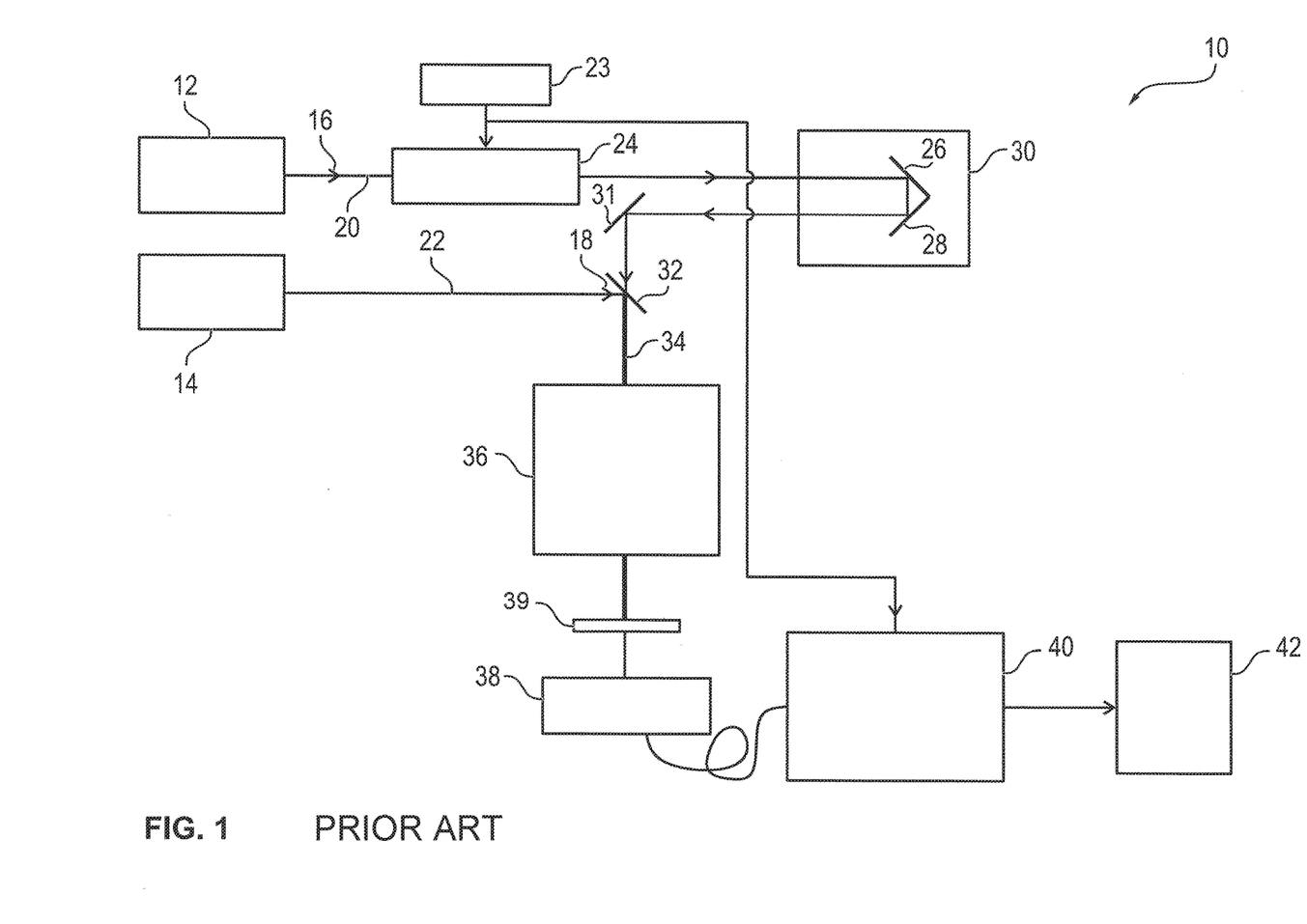
FIG. 1 shows a device not in accordance with the present invention for carrying out the SRS method, as a comparative example.

The SRS imaging device designated in general as 10 in FIG. 1 contains a first pulsed laser light source 12 and a second pulsed laser light source 14. The two pulsed laser light sources 12 and 14 emit pulsed laser beams 16 and 18 respectively along a first light path 20 and a second light path 22. One of these laser beams 16, 18 functions in SRS imaging as a pump beam, and the other laser beam as a Stokes beam. The laser beam that has the lesser wavelength is typically referred to as a "pump beam," while the laser beam having the greater wavelength is referred to as a "Stokes beam."

In the arrangement according to FIG. 1, first laser beam 16 emitted along first light path 20 from pulsed laser light source 12 is amplitude-modulated with the aid of a modulator 24 activated via a high-frequency driver 23, for example an acousto-optic modulator (AOM) or an electro-optic modulator (EOM). The amplitude-modulated laser beam 16 then passes through a delay stage 30 constituted by two mirrors 26, 28 and is then incident onto a mirror 31 that reflects first laser beam 16 toward a dichroic beam splitter 32. Dichroic beam splitter 32 combines first laser beam 16, emitted along first light path 20, with second laser beam 18, emitted along second light path 22, in a shared light path 34. The two laser beams 16 and 18 thus become temporally and spatially superimposed onto one another as a result of delay stage 30 and dichroic mirror 32.

Arranged in shared light path 34 is an optical system 36 that encompasses a confocal microscope optical system having a laser scanning unit. Optical system 36 directs the two mutually superimposed laser beams 16 and 18 onto a sample (not explicitly depicted in FIG. 1).

Device 10 according to FIG. 1 further contains a detector 38 operating in transmission and/or reflection. Arranged in front of detector 38 is an optical filter 39 that blocks first laser beam 16 and directs second laser beam 18 onto detector 38. Detector 38 is electrically connected to an evaluation unit 40 that is in turn coupled to an image generation unit 42.

Laser beams 16 and 18 that are spatially and temporally superimposed on one another interact with the sample in such a way that second laser beam 18 experiences a slight amplitude modulation whose frequency corresponds to the modulation frequency at which modulator 24 amplitude-modulates first laser beam 16. This situation is depicted in FIG. 2.

Figure 2:
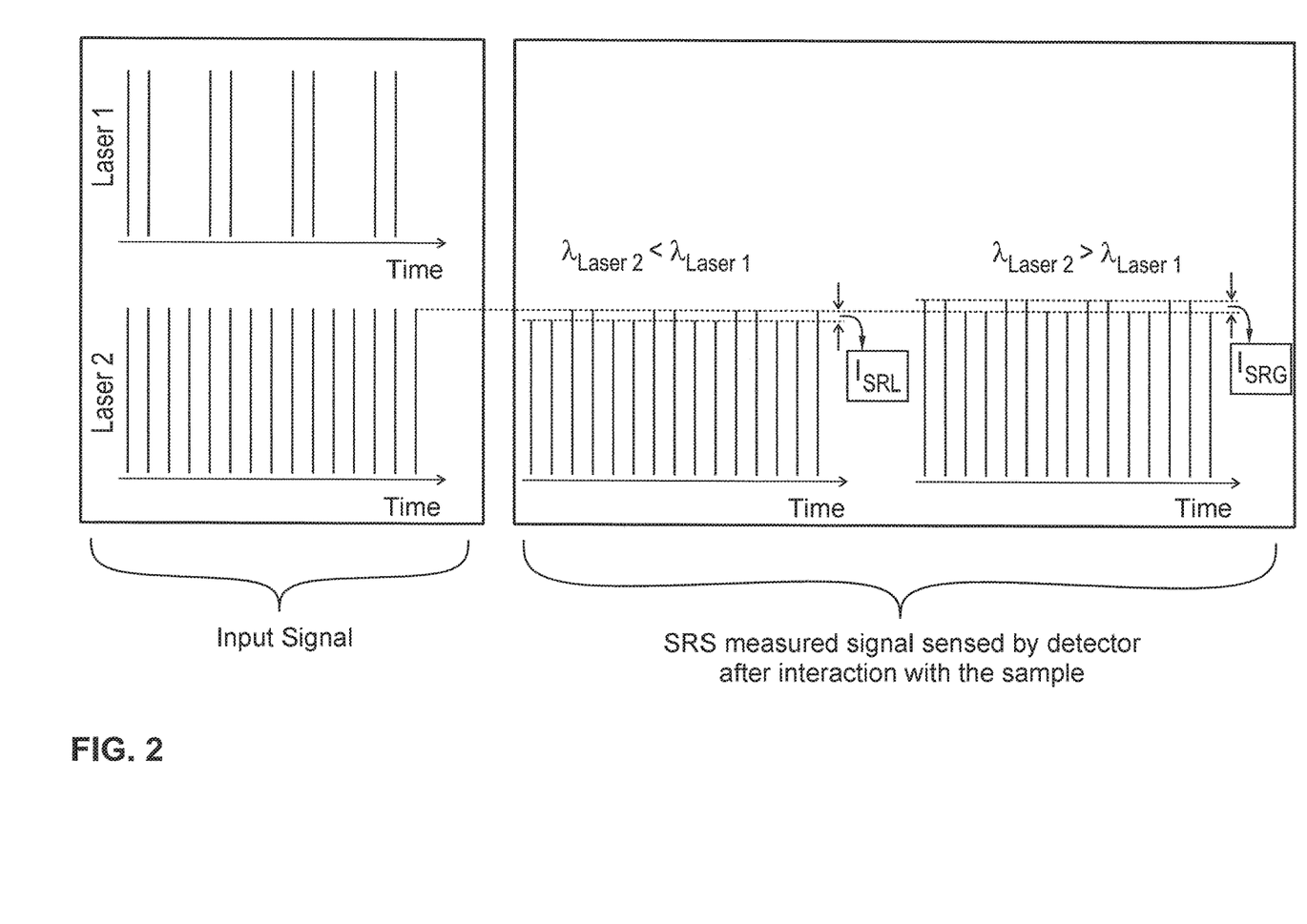
FIG. 2 shows schematic pulse diagrams in order to illustrate how an SRS measured signal is obtained with the comparative device of FIG. 1.

FIG. 2 shows in the left part of the image, in the upper region thereof the pulsed first laser beam emitted by pulsed laser light source 12, and in the lower region thereof the pulsed second laser beam 18 emitted by pulsed laser light source 14. The two laser beams constitute the input signal. The right part of FIG. 2, conversely, shows an SRS measured signal that detector 38 senses as a result of the interaction of the two laser beams 16, 18 with the sample. According to this, second laser beam 18 experiences an intensity gain or an intensity loss as a result of this interaction, depending on which of the two laser beams has the greater wavelength. If the wavelength of second laser beam 18 ($\lambda_{Laser2}$ in FIG. 2) is less than the wavelength of first laser beam 16 ($\lambda_{Laser1}$ in FIG. 2), the result is then an intensity loss that is labeled $I_{SRL}$ in FIG. 2. On the other hand, if the wavelength of second laser beam 18 is greater than that of first laser beam 16, an intensity gain (indicated as $I_{SRG}$ in FIG. 2) then occurs. As is evident from FIG. 2, the intensity loss $I_{SRL}$ or intensity gain $I_{SRG}$ has a modulation frequency that is equal to the frequency of the high-frequency driver signal with which high-frequency driver 23 activates modulator 22. The measured signal according to FIG. 2 which is sensed by detector 38 is demodulated by evaluation unit 40. For this, the high-frequency driver signal with which high-frequency driver 23 activates modulator 22 for the purpose of amplitude modulation of first laser beam 16 is delivered to evaluation unit 40. A demodulation signal generated in this manner is sent by evaluation unit 40 to image generation unit 42 which generates an image signal therefrom, and/or to additional processing units that further process the demodulation signal, for example for purposes of storage or signal analysis.

The following problems occur in the context of comparative device 10 according to FIG. 1: Because of the two pulsed laser light sources 12 and 14, comparative device 10 is extremely sensitive in terms of the delay that must be established between the two laser beams 16 and 18. Stringent requirements also exist in terms of the pulse synchronization that must exist in the context of operation of the two pulsed laser light sources 12, 14. Lastly, arrangements must be made to reliably avoid a time-related cyclical "jitter" that can occur during the operation of pulsed laser light sources 12, 14.

Figure 3:
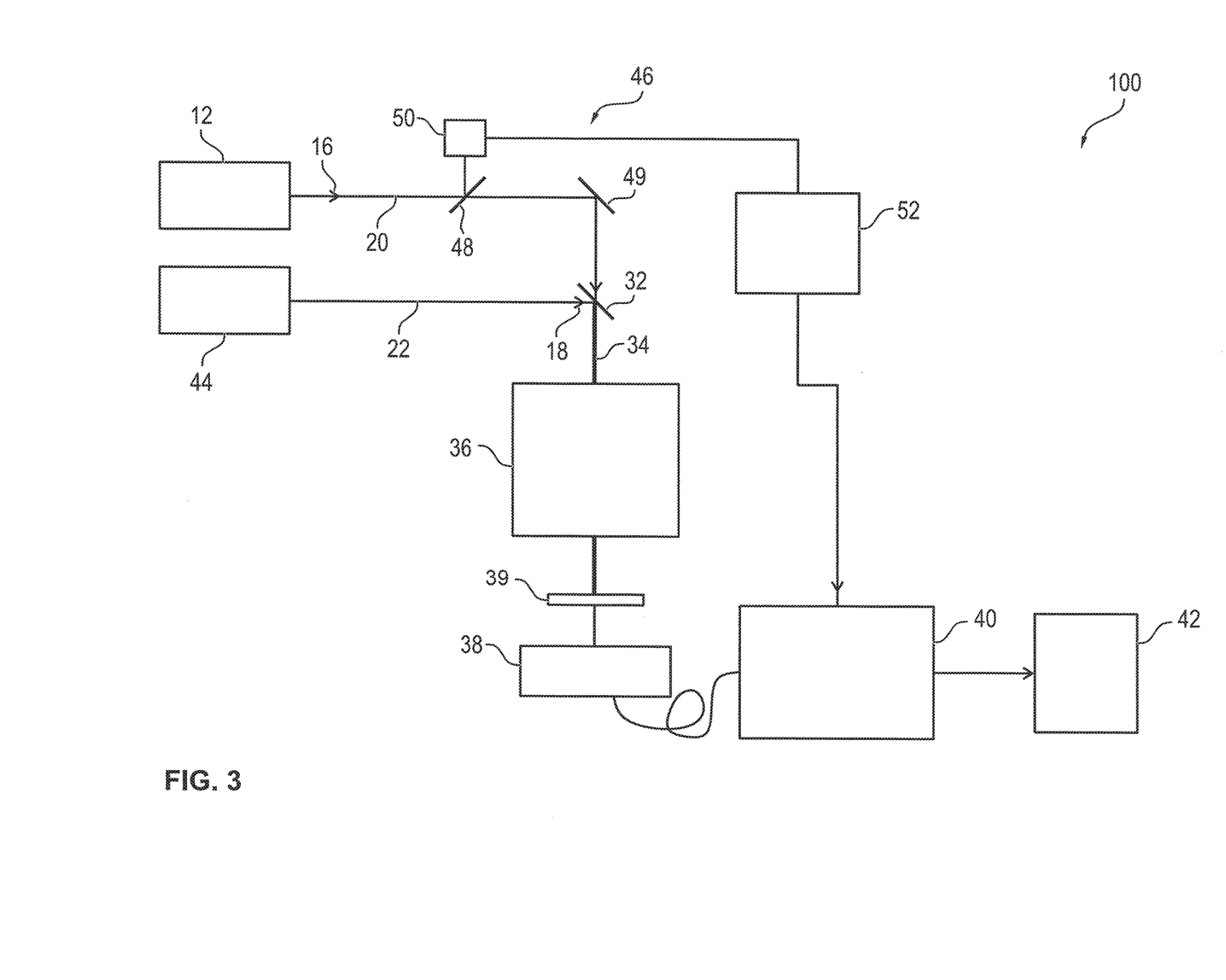
FIG. 3 shows a device according to the present invention for carrying out the SRS method.

FIG. 3 shows a device 100 for carrying out the SRS method, which device is modified according to the present invention with respect to the comparative example according to FIGS. 1 and 2 in order to eliminate the problems recited above. Those aspects in which device 100 according to the present invention shown in FIG. 3 corresponds to the comparative example shown in FIGS. 1 and 2 will not be explained again below. Components that correspond to one another in terms of function and/or configuration are accordingly labeled with the same reference characters.

Device 100 according to the present invention as shown in FIG. 3 differs from comparative device 10 as shown in FIG. 1 substantially in that a continuous laser light source 44, which emits second laser beam 18 in the form of a continuous laser beam, is provided instead of pulsed laser source 14. Device 100 according to the present invention further differs from comparative device 10 in that the components required therein in order to amplitude-modulate and delay first laser beam 16, namely respectively modulator 24 and high-frequency driver 23, and delay stage 30, are omitted.

Device 100 according to the present invention furthermore contains a reference signal generator, labeled overall 46 in FIG. 3, that is constituted by: a beam splitter 48 arranged in first light path 20, a rate detector 50, and a signal shaper 52 that is coupled to evaluation unit 40. Beam splitter 48 is embodied in such a way that it diverts a portion of the pulsed first laser beam 16 out of first light path 20 and delivers it to rate detector 50. The latter senses, from the light signal delivered to it, the pulse repetition rate at which pulsed laser light source 12 is emitting first laser beam 16. Rate detector 50 then outputs an electrical signal, corresponding to the sensed pulse repetition rate, to signal shaper 52, which generates therefrom a reference signal that evaluation unit 40 requires in order to evaluate the SRS measured signal sensed by detector 38.

First laser beam 16 emitted from pulsed laser light source 12 is reflected in first light path 20, at a mirror 49, toward dichroic mirror 32. The latter combines first laser beam 16 and second laser beam 18, emitted from continuous laser light source 44, in shared light path 34. Laser beams 16, 18, spatially superimposed on one another in this manner, are then directed through optical system 36 onto the sample (not explicitly shown in FIG. 3).

As a consequence of the interaction of the two laser beams 16, 18 with the sample, the continuous second laser beam 18 experiences an intensity modulation in the form of an intensity loss or an intensity gain, depending on whether its wavelength is less than or greater than the wavelength of first laser beam 16, the frequency of this intensity modulation being equal to the pulse modulation rate at which pulsed laser light source 12 emits first laser beam 16. This situation is illustrated by the pulse diagrams of FIG. 4.

Figure 4:
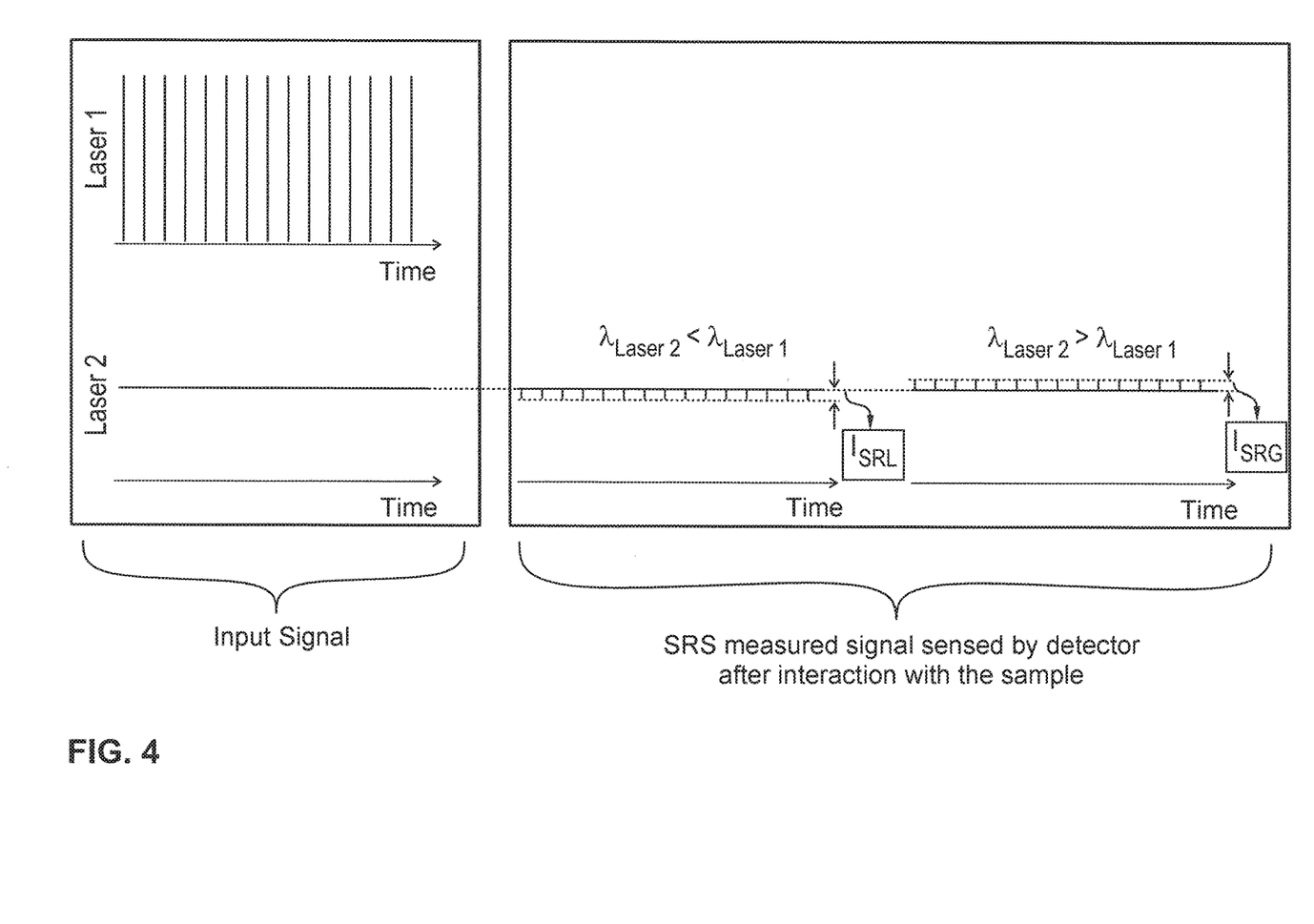
FIG. 4 shows schematic pulse diagrams in order to illustrate how an SRS measured signal is obtained with the device of FIG. 3 according to the present invention.

FIG. 4 shows in the left part of the image, in the upper region thereof the pulsed first laser beam 16 that pulsed laser light source 12 emits, and in the lower region thereof the continuous second laser beam 18 that continuous laser light source 44 emits. The right part of FIG. 2 shows the SRS measured signal sensed by detector 38 as a function of the wavelengths of the two laser beams 16 and 18. If the wavelength of the continuous second laser beam 18 ($\lambda_{Laser2}$ in FIG. 4) is less than the wavelength of the pulsed first laser beam 16 ($\lambda_{Laser1}$ in FIG. 4), second laser beam 18 then experiences an intensity loss that is labeled $I_{SRL}$ in FIG. 4. On the other hand, if the wavelength of the continuous second laser beam 18 is greater than the wavelength of the pulsed first laser beam 16, second laser beam 18 then experiences an intensity gain that is labeled $I_{SRG}$ in FIG. 4.

Detector 38 outputs the sensed SRS measured signal to evaluation unit 40. The latter demodulates the SRS measured signal with the aid of the reference signal that is furnished to it from reference signal generator 46. This demodulation can be accomplished, for example, by way of a lock-in amplification operation. It is self-evident that the embodiment explained with reference to FIGS. 3 and 4 is to be understood merely as an example. This embodiment refers, for example, to utilization of the SRS method. The concept according to the present invention of Raman microscopy imaging with the aid of both a pulsed laser beam and a continuous laser beam is likewise applicable to other methods, for example CARS, CSRS, or RIKES. Upon application of these methods, suitable filters and polarizing elements in the light paths depicted are to be supplemented as applicable in accordance with the specifically selected experimental configuration.

PARTS LIST

10 Comparative device
12 Pulsed source
14 Pulsed source
16 First laser beam
18 Second laser beam
20 First light path
22 Second light path
23 High-frequency driver
24 Modulator
26, 28 Mirror
30 Delay stage
32 Dichroic mirror
34 Shared light path
36 Optical system
38 Detector
39 Optical filter
40 Evaluation unit
42 Image generation unit
44 Continuous source
46 Reference signal generator
48 Beam splitter
50 Rate detector
52 Signal shaper
100 Device

What is claimed is:

1. A Raman microscopy imaging device, comprising:
a first laser light source for emitting a first laser beam having a first wavelength along a first light path;
a second laser light source for emitting a second laser beam having a second wavelength, different from the first wavelength, along a second light path physically separated from the first light path;
a beam combining element for collinearly combining the first and second laser beams in one shared light path directed onto a sample;
a detector for sensing a measured signal on the basis of the first and second laser beams interacting with the sample; and
an evaluation unit for evaluating the measured signal sensed by the detector, wherein
the first laser light source includes a pulsed source, for emitting the first laser beam in the form of a pulsed laser beam, wherein the pulsed source is a femtosecond laser or a picosecond laser;
the second laser light source includes a continuous source, for emitting the second laser beam in the form of a continuous laser beam;
the second laser beam is directed onto the sample combined with the first laser beam without being subjected to any modulation prior to interacting with the sample;
the detector is configured to sense, as a measured signal, an amplitude modulation of the second laser beam caused by interaction of the first laser beam and the second laser beam with the sample; and
the evaluation unit is configured to evaluate the measured signal as a function of a reference signal that corresponds to a pulse repetition rate at which the first laser light source emits the pulsed first laser beam.

2. The Raman microscopy imaging device according to claim 1, further comprising an optical filter, arranged in front of the detector, wherein the optical filter blocks the first laser beam and directs the second laser beam onto the detector.

3. The Raman microscopy imaging device according to claim 1, further comprising a reference signal generator that generates the reference signal, corresponding to the pulse repetition rate, on the basis of the first laser beam emitted from the first laser source and delivers the reference signal to the evaluation unit.

4. The Raman microscopy imaging device according to claim 3, wherein the reference signal generator includes a beam splitter arranged in the first light path for splitting off the first laser beam emitted from the pulsed source, a rate detector for sensing the pulse repetition rate of the pulsed source on the basis of the first laser beam split off by the beam splitter, and a signal shaper for generating the reference signal as a function of the sensed pulse repetition rate.

5. The Raman microscopy imaging device according to claim 1, wherein the evaluation unit is configured to evaluate the measured signal on the basis of a lock-in amplification operation.

6. The Raman microscopy imaging device according to claim 1, wherein the first and/or the second light source is configured to vary the wavelength of the respective laser beam.

7. The Raman microscopy imaging device according to claim 1, further comprising an optical system, arranged in the shared light path, that directs the first and second laser beams onto the sample.

8. The Raman microscopy imaging device according to claim 7, wherein the optical system comprises a confocal microscope optical system having a laser scanner.

9. A Raman microscopy imaging method for Raman microscopy imaging of a sample, comprising the steps of:
emitting a first laser beam having a first wavelength along a first light path;
emitting a second laser beam having a second wavelength, different from the first wavelength, along a second light path physically separated from the first light path;
combining the two laser beams collinearly in one shared light path directed onto a sample;

sensing a measured signal on the basis of the first and second laser beams interacting with the sample; and evaluating the sensed measured signal, wherein the first laser beam is emitted by a pulsed source in the form of a pulsed laser beam, wherein the pulsed source is a femtosecond laser or a picosecond laser;

the second laser beam is emitted in the form of a continuous laser beam;

the second laser beam is directed onto the sample combined with the first laser beam without being subjected to any modulation prior to interacting with the sample; and the measured signal is evaluated as a function of a reference signal that corresponds to a pulse repetition rate at which the pulsed source emits the pulsed first laser beam.

10. The Raman microscopy imaging method according to claim 9, wherein the measured signal is sensed on the basis of a coherent Raman scattering.

11. The Raman microscopy imaging method according to claim 10, wherein the coherent Raman scattering is selected from a group consisting of a stimulated Raman scattering, a coherent Stokes Raman scattering, and a Raman-induced Kerr effect scattering.

* * * * *